United States Patent
Hwang et al.

(10) Patent No.: US 10,092,210 B2
(45) Date of Patent: Oct. 9, 2018

(54) IMPEDANCE MEASURING DEVICE

(71) Applicant: ROEMSYSTEM CORP., Daejeon (KR)

(72) Inventors: Jung Jin Hwang, Sejong-si (KR); Young Dae Seo, Gwangmyeong-si (KR)

( * ) Notice: Subject to any disclaimer, the term of this patent is extended or adjusted under 35 U.S.C. 154(b) by 0 days.

(21) Appl. No.: 15/302,596

(22) PCT Filed: Nov. 9, 2015

(86) PCT No.: PCT/KR2015/011980
§ 371 (c)(1),
(2) Date: Oct. 7, 2016

(87) PCT Pub. No.: WO2016/199987
PCT Pub. Date: Dec. 15, 2016

(65) Prior Publication Data
US 2018/0116545 A1   May 3, 2018

(30) Foreign Application Priority Data

Jun. 9, 2015 (KR) .................. 10-2015-0080991

(51) Int. Cl.
*G01R 27/00* (2006.01)
*A61B 5/053* (2006.01)
*G01R 27/18* (2006.01)
*A61B 5/04* (2006.01)

(52) U.S. Cl.
CPC ............ *A61B 5/053* (2013.01); *A61B 5/04* (2013.01); *G01R 27/18* (2013.01)

(58) Field of Classification Search
CPC ................ A61B 5/04; A61B 5/053–5/0538
USPC .................................................. 324/600
See application file for complete search history.

(56) References Cited

FOREIGN PATENT DOCUMENTS

KR          10-1114671          2/2012

OTHER PUBLICATIONS

English translation of 10-1114671.

*Primary Examiner* — Patrick Assouad
*Assistant Examiner* — Demetrius Pretlow
(74) *Attorney, Agent, or Firm* — Antonio Ha & U.S. Patent, LLC

(57) ABSTRACT

The present invention relates to an impedance measuring device obtaining impedance of portions of an object corresponding to two sensing electrodes by detecting, through the two sensing electrodes, an electrical variation shown on the object as an electrical signal is applied. A detector amplifying each of signals detected through the two sensing electrodes and then differential-operating the amplified signals to generate a signal for obtaining impedance is subjected to a calibration process for adjusting the gain of the amplifiers to reduce in-phase noise added due to an imbalance between the sensing electrodes.

7 Claims, 7 Drawing Sheets

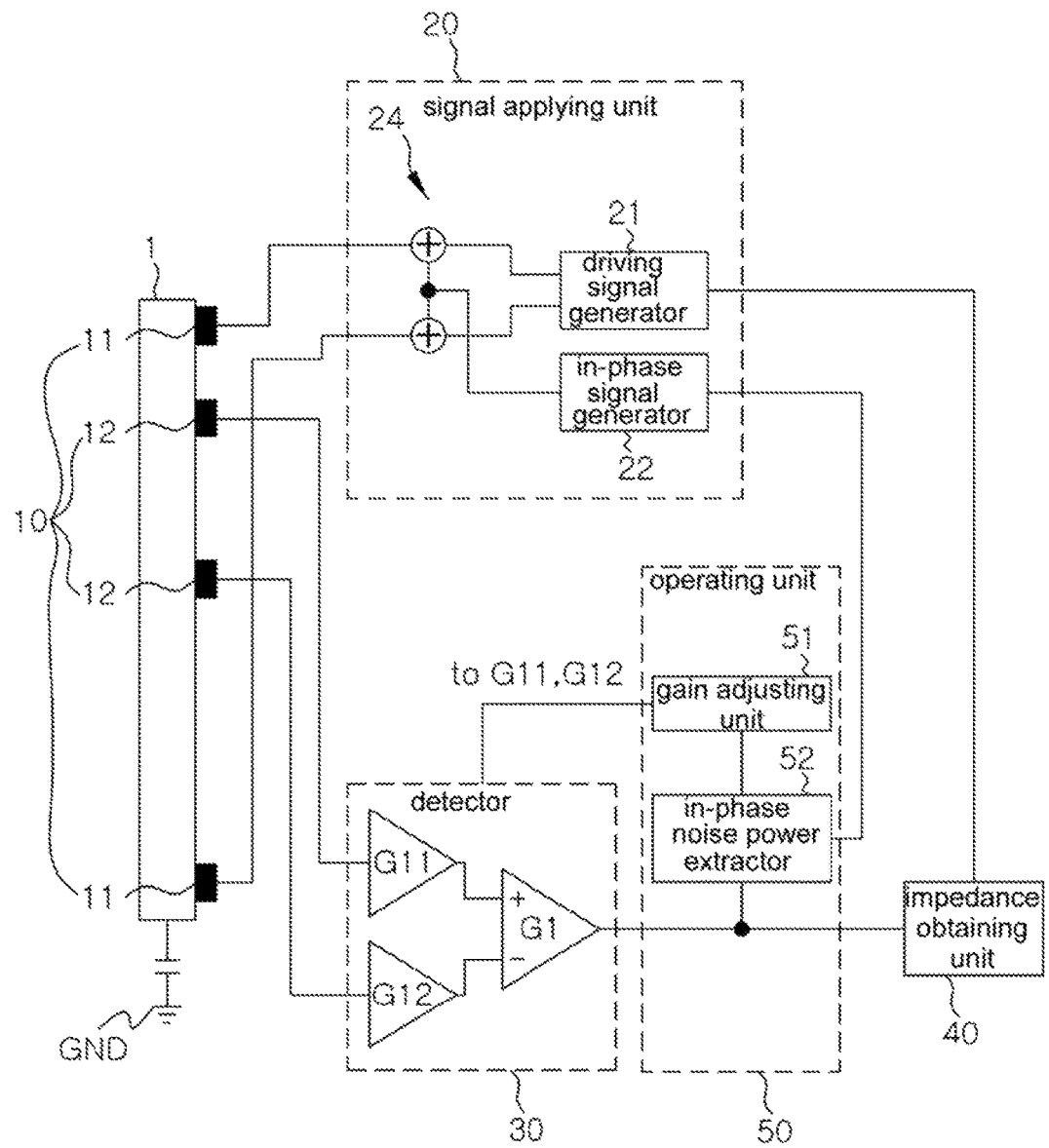

IMPEDANCE MEASURING DEVICE

TECHNICAL FIELD

The present invention relates to an impedance measuring device obtaining impedance of portions of an object corresponding to two sensing electrodes by detecting, through the two sensing electrodes, an electrical variation shown on the object as an electrical signal is applied.

DISCUSSION OF RELATED ART

Measuring impedance of each portion of an object requires an electrical signal to be applied to a path passing through a portion under measurement to detect an electrical change shown on the portion.

For example, the object may include a human body, tissues, cells, proteins, or portions obtained by electrical tomography. The impedance of a portion of the object, which is under impedance measurement, may be obtained by applying an electric current to the portion and measuring an electrical potential at the portion.

As an electrical signal applied to the object, a frequency-swept signal may be used to detect a variation in the terminal-to-terminal electric potential or a variation in phase to obtain more exact impedance information. As disclosed in Korean Patent No. 10-1114671, impedance may be obtained by separating, per frequency component, signals detected by simultaneously applying multiple electrical signals with different frequencies under the superposition principle.

For example, bio impedance may be obtained by attaching a pair of sensing electrodes to an object under measurement, respectively amplifying signals detected from the sensing electrodes, and differential-operating the amplified signals. In this case, an impedance imbalance may occur where the contact impedance between each sensing electrode and the object and the impedance of a path along which the detection signals from the sensing electrodes are conveyed to a device for obtaining impedance differ per sensing electrode. Such impedance imbalance may frequently vary as the object moves or according to the hardness of the adhesive used to attach the sensing electrodes to the object.

As such, an impedance imbalance results in an inaccurate impedance being obtained. Moreover, noise added through each sensing electrode is not eliminated by the differential operator but remains at a high level, causing the impedance much more inaccurate.

Meanwhile, such impedance imbalance may be corrected by measuring contact impedance between each sensing electrode and the object. Such correction, however, is quite burdensome and imprecise, and is difficult to achieve due to frequent variations caused as the human body moves.

PRIOR ART DOCUMENT

Patent Document (Patent Document 1) KR10-114671 B1 (2012 Feb. 2)

SUMMARY

Thus, the present invention addresses an impedance imbalance between a pair of sensing electrodes when measuring the impedance of an object and aims to provide an impedance measuring device capable of obtaining exact impedance for an object by freeing an impedance imbalance between the sensing electrodes in a quick and simplified manner prior to obtaining the impedance of the object.

In order to achieve the above object, the present invention is to provide an impedance measuring device comprising a signal applying unit 20 applying a driving signal for measuring impedance between two driving electrodes 11 with space from each other contacted to an object 1, a detector 30 amplifying, by an amplifier, each of signals detected through two sensing electrodes 12 by applying the driving signal by amplifiers and differential-operating the amplified signal by a differential operator, the two sensing electrodes spaced apart from each other and contacting the object 1, an impedance obtaining unit 40 outputting impedance of the object 1 corresponding to the two sensing electrodes 12 based on an output signal of the detector 30, and the impedance measuring device further comprises an operating unit extracting power of an in-phase noise mixed with the output signal of the detector 30, adjusting a gain of the amplifier of the detector 30 to decrease the power of the in-phase noise, and then obtaining an impedance based on the output signal of the detector obtained by applying the adjusted gain.

The signal applying unit 20 sequentially applies an in-phase signal detected as an in-phase noise through the two sensing electrodes 12 and the driving signal for measuring the impedance to the driving electrode 11. The operating unit extracts the power of an in-phase signal component from the output signal of the detector 30 when applying the in-phase signal, adjusts the gain of the amplifier of the detector 30 to decrease the power of the in-phase signal component, and then obtains the impedance based on the output signal of the detector 30 when applying the driving signal.

The signal applying unit 20 simultaneously applies the driving signal for measuring impedance and an in-phase signal that is different from the driving signal and detected as in-phase noise through the two sensing electrodes 12 to the driving electrodes 11. The operating unit extracts power of an in-phase signal component from the output signal of the detector 30, adjusts the gain of the amplifier of the detector 30 to decrease the power of the in-phase signal component, and then obtains impedance based on the driving signal detected as the output signal of the detector 30.

The in-phase noise is commercial current frequency component.

The detector 30 includes a pair of detectors 30-1 and 30-2 outputting a signal obtained by unequally amplifying the detection signals respectively from the two sensing electrodes 12 by the amplifiers, respectively, and then differential-operating the amplified signals by the differential operator, detection signals relatively highly amplified by the pair of detectors 30-1 and 30-2 being different from each other. The operating unit includes a power normalizer 63 normalizing output signals from the pair of detectors 30-1 and 30-2 so that the power of the in-phase noise becomes the same and an in-phase noise suppressor 64 synthesizing the normalized signals to output an in-phase noise-suppressed signal. The gain of each amplifier in the pair of detectors 30-1 and 30-2 is adjusted to reduce the power of the in-phase noise remaining on the output signal of the in-phase noise suppressor, and the impedance is obtained based on the signal outputted from the in-phase noise suppressor 64 under application of the adjusted gain and a normalization condition obtained when the gain is adjusted.

The in-phase noise suppressor 64 comprises one of a subtractor performing a differential operator and an adder performing addition.

The detector 30 comprises two detectors 30-1 and 30-2 respectively connected to the sensing electrodes 12. The operating unit alternately selects the two detectors 30-1 and 30-2 when adjusting the gain of the amplifier, adjusts the gain of the amplifier in a selected detector until to be lower in in-phase noise of the output signal than an unselected detector, and then selects a detector presenting a relatively lower in-phase noise of the two detectors and obtains the impedance based on the output signal of the selected detector.

According to the present invention having the above-described features, the calibration for adjusting the gain of the amplifiers in the detector is performed to minimize in-phase noise added to the sensing electrodes by in-phase signals forced to be applied to the object or in-phase noise shown on the object as if it is a commercial electricity frequency component, thereby addressing an impedance imbalance between the sensing electrodes. Thus, exact impedance for the object may be obtained after the calibration. Further, the calibration is carried out using the in-phase signals flowed and detected through the sensing electrodes, and may thus be quickly and accurately done. Further, although the impedance imbalance between the sensing electrodes is frequently varied, the impedance of the object may be obtained with accuracy.

BRIEF DESCRIPTION OF THE DRAWINGS

FIG. 7 is a block diagram specifically illustrating an impedance measuring device according to a sixth embodiment of the present invention.

DETAILED DESCRIPTION OF EXEMPLARY EMBODIMENTS

Hereinafter, preferred embodiments of the present invention are described with reference to the accompanying drawings to be easily practiced by one of ordinary skill in the art.

Known functions related to techniques for obtaining impedance information by applying a frequency-swept signal to an object under examination or known configurations making the gist of the invention unnecessarily unclear if described in detail are excluded from the detailed description of the embodiments of the present invention.

Figure 1:
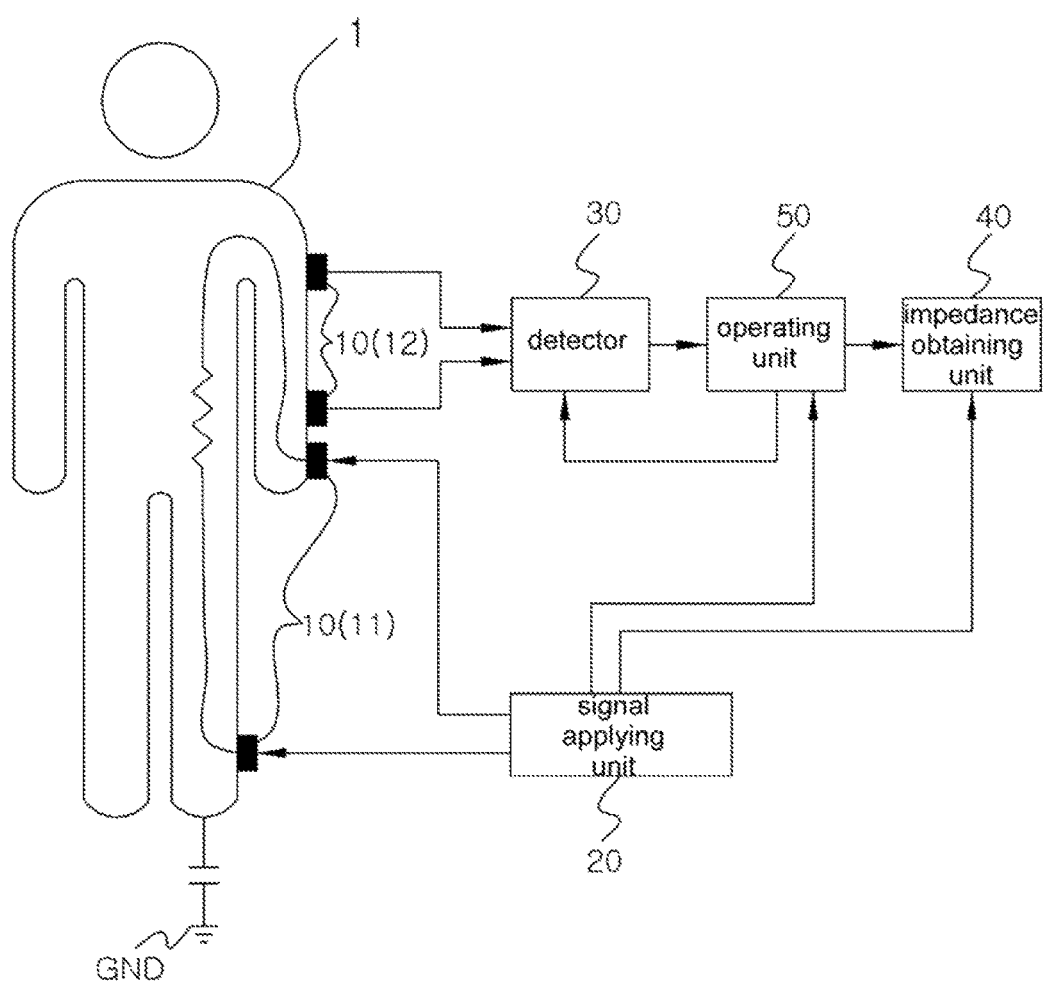
FIG. 1 is a block diagram schematically illustrating an impedance measuring device according to a first embodiment of the present invention.

Further, as used herein, the term "object under measurement" (simply, "object") may mean a human body as shown in FIG. 1, or the "object" may include biological tissues, cells, proteins, areas imaged by electrical tomography, or liquids, or any target of per-portion impedance measurement.

Figure 2:
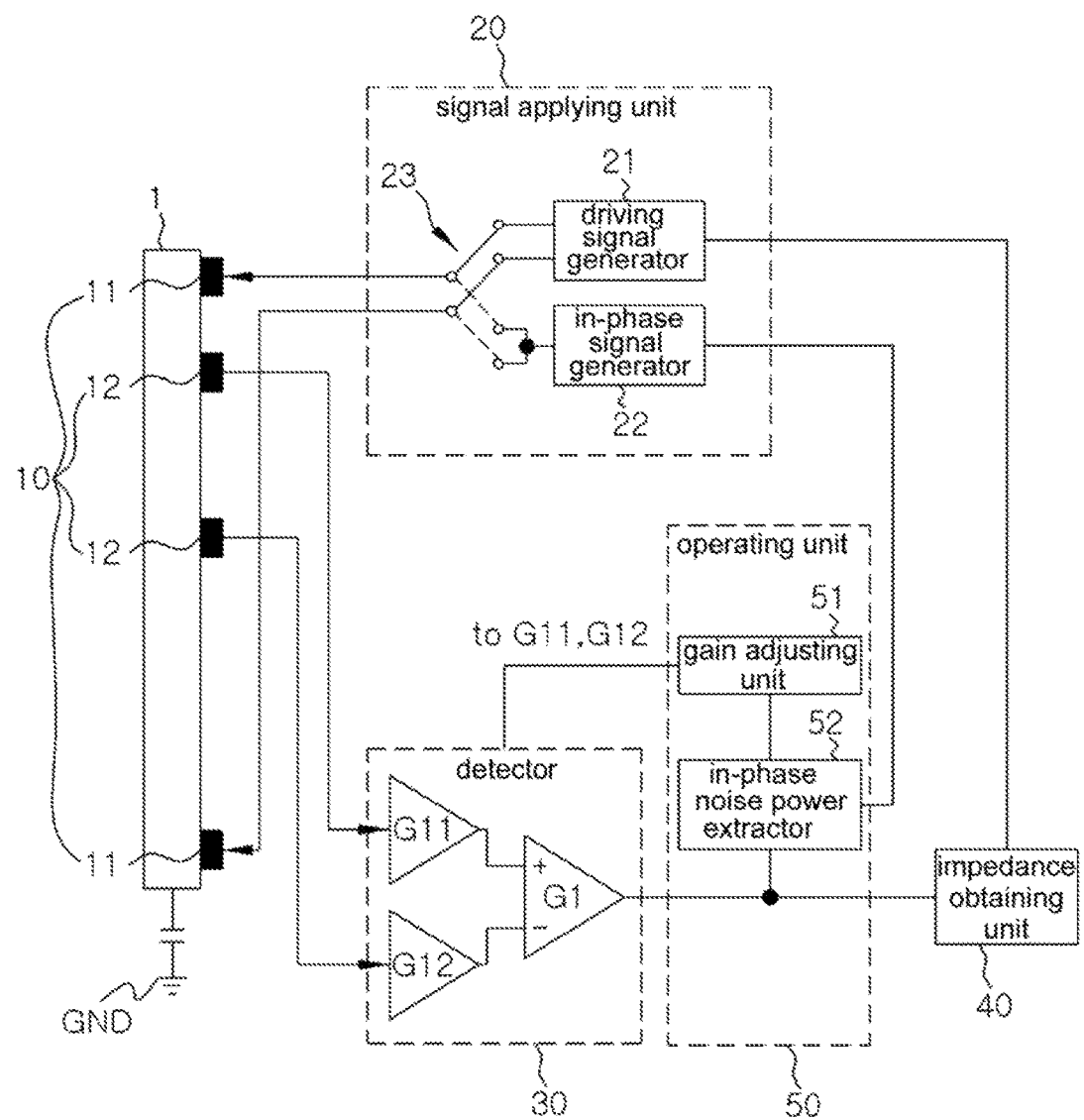
FIG. 2 is a block diagram specifically illustrating the impedance measuring device according to the first embodiment of the present invention.

FIG. 1 is a block diagram schematically illustrating an impedance measuring device according to a first embodiment of the present invention, and FIG. 2 is a block diagram specifically illustrating the impedance measuring device.

According to the first embodiment of the present invention, the impedance measuring device comprises an electrode 10, a signal applying unit 20, a detector 30, an operating unit 50, and an impedance obtaining unit 40.

There may be provided a plurality of electrodes 10 that contact an object 1 and spaced apart from each other and that include two driving electrodes 11 connected to the signal applying unit 20 and two sensing electrodes 12 connected to the detector 30. The same electrode may be used as the driving electrode 11 and the sensing electrode 12.

Here, when bringing the two driving electrodes 11 and two sensing electrodes 12 in contact to the object 1, an influence by signals applied to the two driving electrodes 11 is detected by the two sensing electrodes so that a characteristic for a section between portions contacted by the two sensing electrodes 12 among portions of the object 1 should be able to be obtained as signals detected by the two sensing electrodes 12. For example, when electric currents, which are driving signals, are flowed to the two driving electrodes 11, the two sensing electrodes 12 are required to be in contact with the object 1, spaced apart from each other at an interval on the path along which the currents flow, so that the impedance between the portions contacted by the two sensing electrodes 12 may be obtained by measuring a potential difference by a voltage drop from electric potentials at the two sensing electrodes.

The signal applying unit 20 is a component to apply the driving signals for measuring impedance to the two driving electrodes 11. According to the first embodiment of the present invention, the signal applying unit 20 comprises a driving signal generator 21 generating the driving signals and an in-phase signal generator 22 generating in-phase signals that are detected as in-phase noise with the same phase of waveform on the two sensing electrodes 12, and the signal applying unit 20 selectively applies the driving signals and the in-phase signals to the two driving electrodes 11 by a switch 23.

According to the first embodiment of the present invention, the switch 23 sequentially applies the in-phase signals and the driving signals to the driving electrodes 11. In other words, the in-phase signals are applied before applying the driving signals to the object 1, thereby allowing the detector 30 to be calibrated based on the in-phase signals as described below.

Here, the in-phase signals may employ signals with a specific frequency component or specific pattern. The in-phase signal generator 22 applies the in-phase signals to between the driving electrodes 11 and a ground (GND). Here, the ground (GND) may be, e.g., air around the object 1 when the present invention is applied to a wearable product and may typically be a phantom ground (PHANTOM GND) with a capacitance component. The in-phase signals may be configured to be applied to only one of the two driving electrodes 11.

The detector 30 comprises two amplifiers G11 and G12 respectively connecting to the two sensing electrodes 12 and amplifying the signals detected from the sensing electrodes 12 and a differential operator G1 differential-amplifying and outputting the signals amplified by the two amplifiers G11 and G12. In other words, the detector 30 obtains a difference between electric signals detected from the portions of the object 1 contacted by the two sensing electrodes 12 by signal amplification followed by a differential operation. Here, the two amplifiers G11 and G12 are configured to be adjusted and varied by the operating unit 50.

The operating unit 50 is operated when the signal applying unit 20 applies the in-phase signals to the driving electrodes 11. The operating unit 50 comprises an in-phase noise power extractor 52 extracting the power of an in-phase noise corresponding to the in-phase signal from a signal output from the detector 30, i.e., an output signal of the differential operator G and a gain adjusting unit SI adjusting the gain of the amplifiers G11 and G12 of the detector 30 to decrease the in-phase noise extracted by the in-phase noise power extractor 52.

When the in-phase signal applied by the signal applying unit 20 has a specific frequency component (e.g., a commercial frequency, 60 Hz, component), the in-phase noise power extractor 52 is configured to extract the corresponding frequency component from the output signal of the detector 30, and when the applied in-phase signal is a signal with a specific pattern, the in-phase noise power extractor 52 is configured to obtain the power of the in-phase noise by a correlation analysis between the applied in-phase signal and the output signal of the detector 30.

Substantially, since a difference of the power of in-phase noise mixed with a signal input to the differential operator G11 is required to be minimized in order to minimize the power of in-phase noise mixed with an output signal of the differential operator G1, the operating unit 50 adjusts the amplifiers G11 and G12 to allow the in-phase noise mixed with the signal detected by each of the two sensing electrodes 12 to be the same.

Further, in order to gain precisely reflect the difference between the signals detected from the two sensing electrodes 12 to an output signal of the detector 30 although the gain of the amplifiers G11 and G12 is changed, the gain is changed in such a manner as to increase gain the gain of one of the two amplifiers G11 and G12 while decreasing the gain of the other. For example, if the power of in-phase noise is increased with the gain up for one of the amplifiers and down for the other, the gain allowing the power of in-phase noise to decrease is traced by reversing the direction in which the gain varies for each amplifier.

The operation of adjusting the gain of the amplifiers G11 and G12 may be maintained while applying the in-phase signal to the driving electrodes 11, or the operation may be stopped when reaching a preset convergence condition. Here, the preset convergence condition may include a condition where the power of in-phase noise is reduced to a preset value or less or a condition where, despite the gain adjustment, a ratio or degree by which the power of in-phase noise decreases is small enough to be smaller than a preset ratio or degree.

The two sensing electrodes 12 may undergo a difference in contact resistance depending on the state of contact with the object 1 and a difference in impedance of electric wires used for connection with the detector 30. Even though impedance is obtained by differential-operating signals detected through the two sensing electrodes 12 in the state that such impedance imbalance between the sensing electrodes 12 occurs, in-phase noise (here, noise not by in-phase signal applied by the signal applying unit) flowed to the two sensing electrodes 12 is not removed by the detector 30 but remains on an output signal of the detector 30, and electric signals reflecting an influence by the impedance of the object on the object contacted by the two sensing electrodes 12 are subjected to the differential operation, while unequally transferred to the detector 30, thus making it impossible to exactly obtain impedance.

Therefore, the present invention addresses the imbalance issue by performing a calibration process to adjust the gain of each amplifier G11 and G12 of the detector 30 before measuring impedance even though impedance is imbalanced between the two sensing electrodes 12. Further, precise impedance is obtained by obtaining impedance using the calibrated detector 30. Of course, when a driving signal is applied to the driving electrode 11, an output signal of the detector 30 is a signal obtained by applying a calibrated state.

The impedance obtaining unit 40 produces the impedance of portions of the object corresponding to the two sensing electrodes 12 based on an output signal of the detector 30 when applying the driving signal to the driving electrode 11.

For example, as the driving signal, a signal applied while frequency-swept comes in use. A phase variation and power variation in the signal output from the detector 30 may be extracted by the frequency sweeping to obtain an impedance characteristic of the corresponding portion of the object between the two sensing electrodes 12. Techniques for obtaining the impedance characteristic are known in the art, and no further detailed description thereof is given.

Meanwhile, according to the first embodiment of the present invention, rather than including the in-phase signal generator 22 in the signal applying unit 20, a commercial frequency component (a 60 Hz component in Korea) shown on the object 1 may be taken as the in-phase noise to adjust the gain of the detector 30. For example, since a commercial frequency component may be detected through the sensing electrodes 12 from the human body by commercial frequency electricity used for an ambient electronic/electric product, the commercial frequency in-phase noise detected through the sensing electrodes 12 is put to use without applying a separate in-phase signal to the object. In this case, the switch 23 operates to apply the driving signals to the driving electrodes 11 only when impedance is obtained. However, it is preferred to provide the in-phase signal generator 22 so that the detector 30 may be calibrated even when a very weak or no commercial frequency component is detected from the object.

Figure 3:
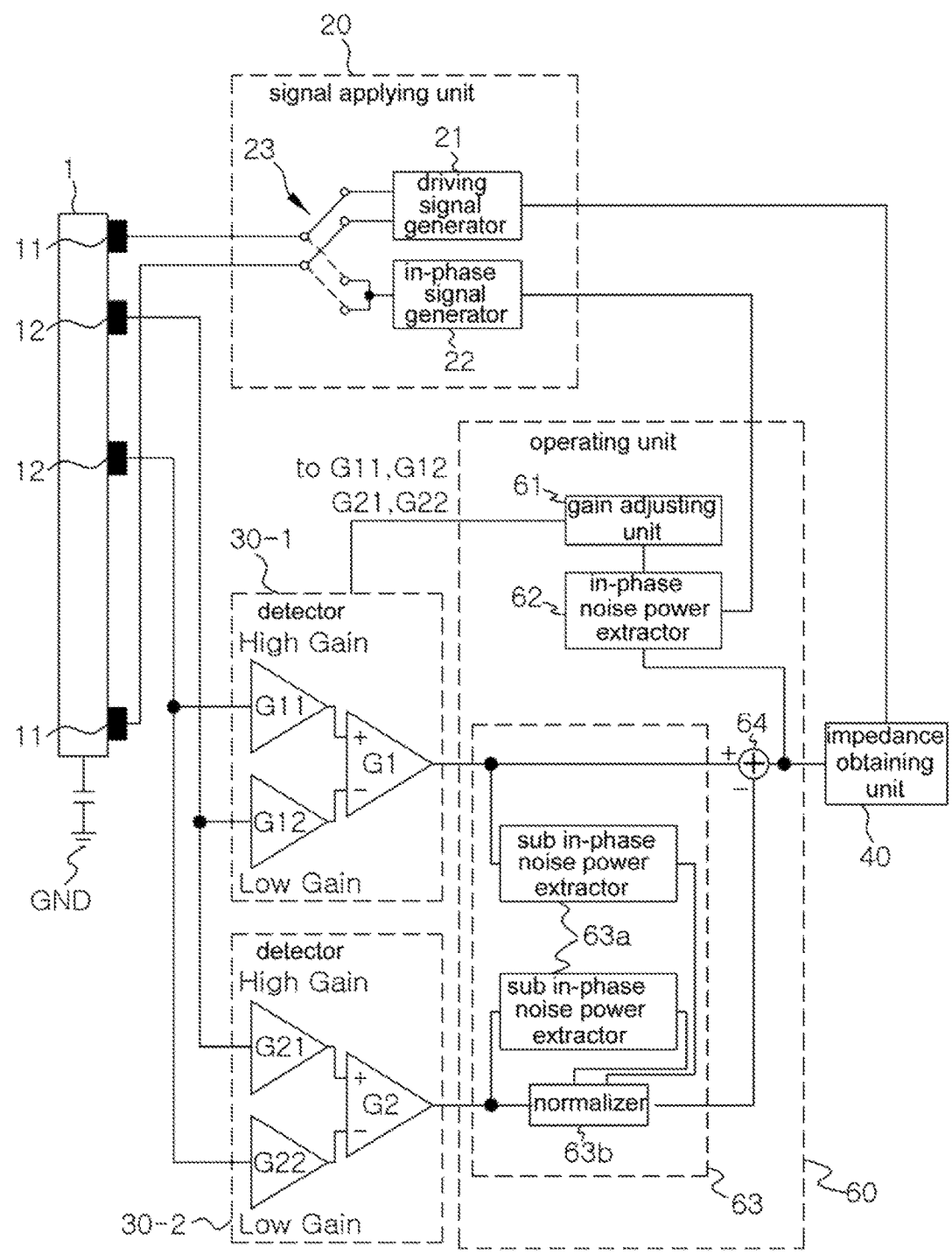
FIG. 3 is a block diagram specifically illustrating an impedance measuring device according to a second embodiment of the present invention.

FIG. 3 is a block diagram specifically illustrating an impedance measuring device according to a second embodiment of the present invention.

For the second embodiment, the pair of detectors 30-1 and 30-2 and operating unit 60 as components different from the first embodiment of the present invention are described.

According to the second embodiment of the present invention, there are two detectors 30 including a first detector 30-1 and a second detector 30-2 in which before differential-operated by a differential operator, detection signals of two sensing electrodes 12 are unequally amplified by their respective corresponding amplifiers so that one of the detection signals of the sensing electrodes may be amplified to have a relatively higher gain than the other detection signal of the sensing electrodes.

Further, a detection signal of the sensing electrode detected to have a relatively higher gain by the first detector 30-1 is rendered to be different from a detection signal of the sensing electrode detected to have a relatively higher gain by the second detector 30-2. In other words, the first detector 30-1 and the second detector 30-2 respectively amplify different detection signals to have relatively higher gains to force the detection signals to have imbalanced magnitudes.

As such, when first detector 30-1 and the second detector 30-2 perform such imbalanced amplification in a reversed manner with respect to each other and then differential operations, if unequally amplified gains are adjusted to suitable values, a signal from which in-phase noise has been suppressed may be obtained by a power normalizer 63 and in-phase noise suppressor 64 described below.

Here, the suitable values of the gains are values at which signals are outputted from both the detectors 30-1 and 30-2 as follows. In other words, under the situation where the in-phase noises mixed with the detection signals differ from each other due to the impedance imbalance between the two sensing electrodes 12, one of the detectors amplifies the relatively higher of the in-phase noises to a larger extent than that of the relatively lower of the in-phase noises so that the in-phase noise phase difference becomes larger and then performs a differential operation, whereas the other detector amplifies the relatively lower of the in-phase noises to a larger extent than that of the relatively higher of the in-phase noises and then performs a differential operation.

If the gain is adjusted so, although a difference in power between the in-phase noises mixed with both the detection signals changes, the phase relation between in-phase noises mixed with output signals of both the detectors is not changed.

Specifically, if the input terminals of the differential amplifiers G1 and G2 respectively included in the detectors 30-1 and 30-2, which receive the detection signal amplified to the relatively larger extent, are rendered to have the same polarity, the in-phase noises mixed with signals outputted from the detectors 30-1 and 30-2 become in-phase, and if the input terminals of the differential amplifiers G1 and G2 of the detectors 30-1 and 30-2, which receive the detection signal amplified to the relatively larger extent have opposite polarities, the in-phase noises mixed with signals outputted from the detectors 30-1 and 30-2 are caused to have different phases from each other.

This is described in greater detail with reference to an embodiment as illustrated in FIG. 3.

In the first detector 30-1, one sensing electrode detection signal is amplified by the amplifier G11 to a high gain and is then inputted to a (+) input terminal of the differential operator G1 while the other sensing electrode detection signal is amplified by the amplifier G12 to a low gain and is then inputted to a (−) input terminal of the differential operator G1.

On the contrary, in the second detector 30-2, one sensing electrode detection signal is amplified by the amplifier G22 to a low gain and is then inputted to a (−) input terminal of the differential operator G2 while the other sensing electrode detection signal is amplified by the amplifier G21 to a high gain and is then inputted to a (+) input terminal of the differential operator G2.

In other words, the detection signal amplified to the high gain in the detector 30-1 and the detection signal amplified to the high gain in the he detector 30-2 are different from each other. The polarity of the input of the detection signal amplified to the high gain in the differential operator G1 of the detector 30-1 is the same as the polarity of the input of the detection signal amplified to the high gain in the differential operator G2 of the detector 30-2.

Here, the low gain may be set to, e.g., an extent for amplifying a weak signal detected through the sensing electrode 12 to power enough for signal processing, and the high gain may be set to a value higher than the low gain, and the high gain may be an amplification gain enough to allow the relatively lower of the in-phase noises mixed with both the detection signals due to the impedance imbalance between both the electrodes to be larger than the relatively lower of the in-phase noises. imbalance Thus, the in-phase noise mixed with the output signal of the differential operator G1 of the first detector 30-1 and the in-phase noise mixed with the output signal of the differential operator G2 of the first detector 30-2 become same.

With reference to FIG. 3, the operating unit 60 comprises a gain adjusting unit 61, an in-phase noise power extractor 62, a power normalizer 63, and an in-phase noise suppressor 64.

First, the power normalizer 63 normalizes the output signals of the first detector 30-1 and the second detector 30-2, which have been rendered to have the same in-phase noise phase, to have the same in-phase noise power.

According to a specific embodiment, the power normalizer 63 comprises two sub in-phase noise power extractors 63a for extracting the power of the in-phase noise mixed with the output signal of the detector 30-1 and the power of the in-phase noise mixed with the output signal of the detector 30-2 to obtain a power ratio of the in-phase noises mixed with both the output signals and a normalizer 63b amplifying any one of output signals of the first detector 30-1 and the second detector 30-2 according to the in-phase noise power ratio to enable both the output signals to become signals mixed with the same power of in-phase noise.

With reference to FIG. 3, a ratio of the power of the in-phase noise mixed with the output signal of the first detector 30-1 to the power of the in-phase noise mixed with the output signal of the second detector 30-2 is obtained, and the ratio is multiplied by the output signal of the second detector 30-2.

In this case, since the output signal of the second detector 30-2 is normalized and reduced from the output signal of the first detector 30-1 as described below, the gain of the amplifier G21 amplifying to a relatively higher extent in the second detector 30-2 may be relatively lower than the gain of the amplifier G11 amplifying to a relatively higher extent in the first detector 30-1.

The in-phase noise suppressor 64 synthesizes both the signals normalized by the power normalizer 63 and outputs a signal from which the in-phase noise has been removed.

According to an embodiment shown in FIG. 3, since the in-phase noise mixed with the output signal of the first detector 30-1 and the in-phase noise mixed with the output signal of the second detector 30-2 have the same phase, the in-phase noise suppressor 64 is configured as a subtractor differential-operating both the normalized signals to output a signal where in-phase noises of the same phase have been removed by differential operation and a difference between signals that are not of the same phase is shown. Thus, an output signal of the in-phase noise suppressor 64 is a signal corresponding to the difference between signals individually detected through the two sensing electrodes 12 and having flowed in-phase noise suppressed therefrom.

Meanwhile, from a circuitry point of view, the power normalizer 63 and in-phase noise suppressor 64 may be regarded as obtaining a bio-signal in a digital signal processing area. Further, the first detector 30-1 and second detector 30-2 may be considered to analog signal-process the detection signals from the wo sensing electrodes 12 and then convert into digital signals so that digital signal processing may be performed at an end. Here, the conversion into the digital signals may be possible by configuring the circuit to adding an A/D conversion function to the configuration of the differential operators provided in the first detector 30-1 and the second detector 30-2.

Further, while the gain of the amplifiers included in the first detector 30-1 and second detector 30-2 may be determined to be a suitable, fixed value to fit the extent of impedance imbalance that may occur between the two sensing electrodes 12, the gain may not be limited to a particular extent as the impedance imbalance worsens due to a movement of the human body. Further, the gain is preferably adjusted to a more suitable value.

Thus, according to an embodiment of the present invention, a gain adjusting unit 61 and in-phase noise power extractor 62 are included.

The in-phase noise power extractor 62 extracts the power of in-phase noise remaining on a signal outputted from the in-phase noise suppressor 64.

The gain adjusting unit 61 adjusts the gain of the amplifiers of the first detector 30-1 and second detector 30-2 to reduce the power of in-phase noise extracted by the in-phase noise power extractor 62.

For example, if the phases of in-phase noises mixed with output signals of the first detector 30-1 and second detector 30-2 are not same, although the in-phase noises are normalized and then differential-operated, the in-phase noises are not removed but remains with high power. In this case, the gain of amplifiers is adjusted by the gain adjusting unit 61 so that phases will be the same. As another example, if the power of the in-phase noise mixed with an output signal from one of the first detector 30-1 and second detector 30-2 is very weak, power normalization might not be sufficiently performed due to an error in a power measuring process. Also in this case, the gain of the amplifiers is adjusted so that an in-phase noise-suppressed signal may be obtained by the power normalization followed by the differential operation.

When the gain of the amplifiers of the first detector 30-1 and second detector 30-2 is adjusted, the imbalance amplification condition should be maintained as described above. Further, such a scheme may be adopted as to vary the gain until the power of the remaining in-phase noise is removed by repeating the process of identifying the power of the remaining in-phase noise while adjusting the gain to a predetermined degree.

As described above, according to the second embodiment of the present invention, detection signals of the two sensing electrodes 12 in each of the detectors 30-1 and 30-2 are unequally amplified by the amplifiers and are then differential-operated through the differential operator, obtaining an output signal, and the detection signals relatively highly amplified by the imbalance amplification of the detectors 30-1 and 30-2 are made to be different from each other. The operating unit comprises the power normalizer 63 normalizing the output signals of the pair of detectors 30-1 and 30-2 to have the same in-phase noise power and the in-phase noise suppressor 64 synthesizing the normalized signals to output a signal from which in-phase noise has been suppressed.

Further, the gain of each amplifier in the pair of detectors 30-1 and 30-2 is adjusted so that the power of in-phase noise remaining on the output signal from the in-phase noise suppressor 64 is reduced while the in-phase signals are applied to the driving electrodes 11. If the application of the in-phase signals stops, the gain of the amplifiers at the time that the application of the in-phase signals stops remains unchanged, and the normalization condition of the power normalizer 63 at this time is also maintained. Here, according to the embodiment shown in FIG. 3, the normalization condition is a ratio obtained by dividing the power of the in-phase noised mixed with the output signal from the first detector 30-1 by the power of the in-phase noise mixed with the output power from the second detector 30-2 at the time the in-phase signals stop being applied. Of course, when the power of in-phase noise remaining on the output signal from the in-phase noise suppressor 64 reaches a convergence condition, the gain of the amplifiers and the normalization condition of the power normalizer 63 remain the ones obtained at the time of reaching the convergence condition.

Subsequently, when the driving signals are applied to the driving electrodes 11, the signal outputted from the in-phase noise suppressor 64 with the gain of the amplifiers and the normalization condition of the power normalizer 63 applied remaining unchanged is transferred to the impedance obtaining unit 40. Thus, human body impedance is obtained based on a signal obtained with impedance imbalance between the sensing electrodes 12 eliminated.

Figure 4:
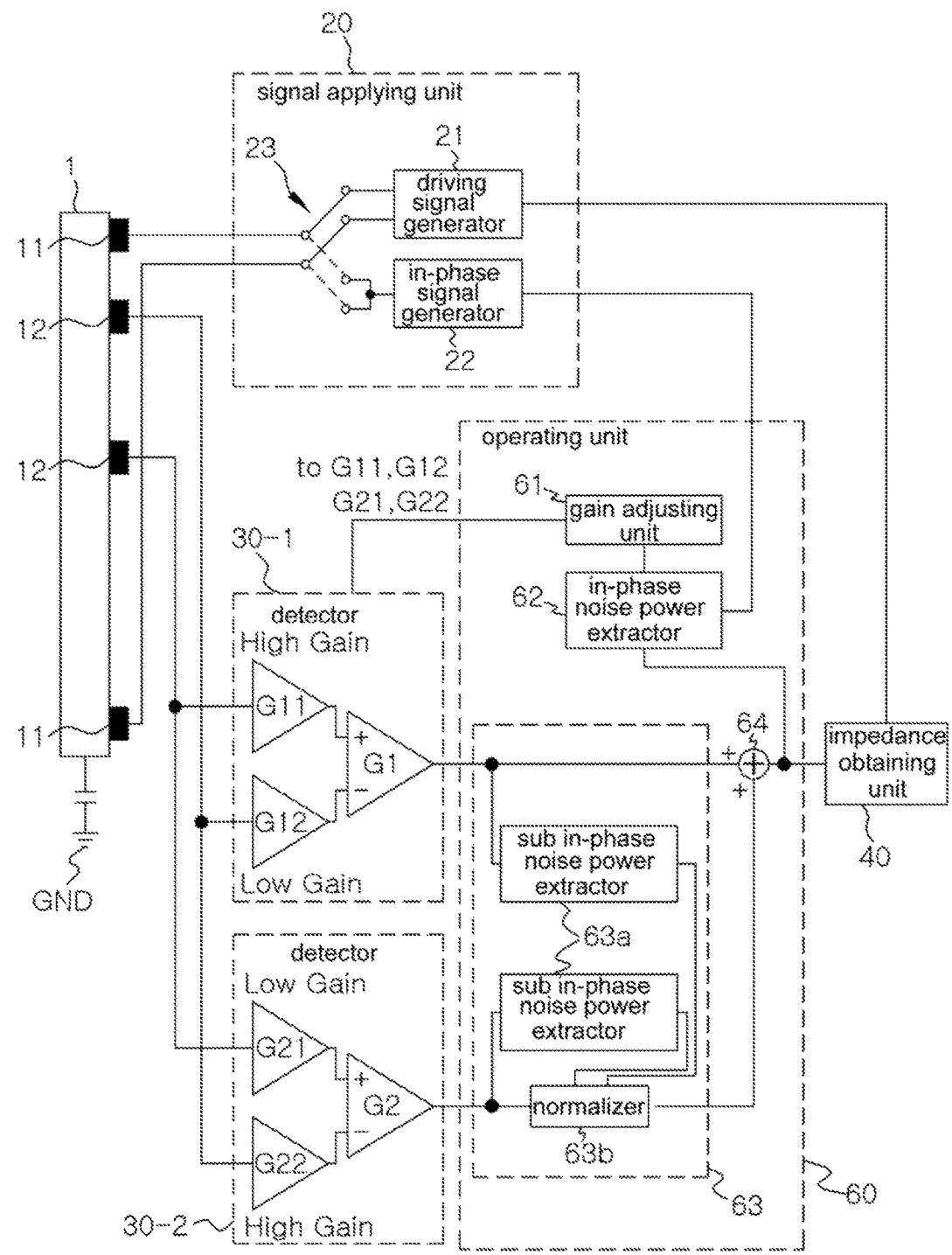
FIG. 4 is a block diagram specifically illustrating an impedance measuring device according to a third embodiment of the present invention.

FIG. 4 is a block diagram specifically illustrating an impedance measuring device according to the third embodiment of the present invention.

According to the third embodiment shown in FIG. 4, a first detector 30-1, a second detector 30-2, and an in-phase noise suppressor 64 have a different configuration from that in the second embodiment described with reference to FIG. 3.

First, the first detector 30-1 and second detector 30-2 are described. The input terminal of the differential operator in the first detector 30-1, which receives a relatively highly amplified detection signal, and the input terminal of the differential operator in the second detector 30-2, which receives a relatively highly amplified detection signal, are reverse polarities with respect to each other.

Specifically, it is the same as in the second embodiment that a relatively highly amplified one of detection signals from the two sensing electrodes 12 in the first detector 30-1 differs from a relatively highly amplified one of detection signals from the two sensing electrodes 12 in the second detector 30-2, but the third embodiment differs from the second embodiment in that the input terminal of the differential operator G1, to which the relatively highly amplified detection signal is input for differential operation in the first detector 30-1, has a polarity opposite to the polarity of the input terminal of the differential operator G2, to which the relatively highly amplified detection signal is input for differential operation in the second detector 30-2.

Therefore, since the phase of in-phase noise mixed with an output signal of the first detector 30-1 is reverse to the phase of in-phase noise mixed with an output signal of the second detector 30-2, the in-phase noise suppressor 64 is configured as an adder adding both the output signals to suppress the in-phase noise.

In other words, according to the second and third embodiment, if the signal processing of the detection signals from the two sensing electrodes 12 meets the condition that the detection signal relatively highly amplified in the first detector 30-1 is rendered to differ from the detection signal relatively highly amplified in the second detector 30-2, although the phase of the in-phase noise mixed with the output signal from the first detector 30-1 and the in-phase noise mixed with the output signal from the second detector 30-2 may be changed according to configurations of the first detector 30-1 and the second detector 30-2, an in-phase noise-suppressed biometric signal may be obtained by configuring the in-phase noise suppressor 64 to fit the phase.

Meanwhile, upon uneven amplification in the first detector 30-1 and second detector 30-2, followed by a differential operation, the in-phase noise mixed with the output signal from the first detector 30-1 and the in-phase noise mixed with the output signal from the second detector 30-2 may have the same phase or opposite phases (180-degree phase difference) depending on the uneven gains.

Thus, the in-phase noise suppressor 64 may be configured to operate as both an adder and operator (subtractor) so that in case in-phase noise obtained when it operates in either way remains, it may switch into the other operation. Here, if in-phase noise remains when the in-phase noise suppressor 64 operates as an adder, the in-phase noise suppressor 64 may switch to operate as a differential operator, and if in-phase noise remains when the in-phase noise suppressor 64 operates as a differential operator, the in-phase noise suppressor 64 may switch to operate as an adder.

As set forth above, even when an impedance imbalance between the two sensing electrodes 12 occurs, an in-phase noise-suppressed signal may be obtained from signals acquired by amplifying detection signals from the two sensing electrodes 12 by the pair of detectors 30-1 and 30-2 and then differential-operating the amplified signals. Further, since in-phase noise may be suppressed by adjusting the gain of the amplifiers in the pair of detectors 30-1 and 30-2, although the difference in impedance between the two sensing electrodes 12 varies from time to time, an in-phase noise-suppressed signal may swiftly be obtained, and even when the human body moves, an in-phase noise-suppressed signal may be obtained as well. Thus, the operating unit and detectors may quickly be calibrated to address the impedance imbalance between the sensing electrodes, and an exact human body impedance value may be obtained.

Figure 5:
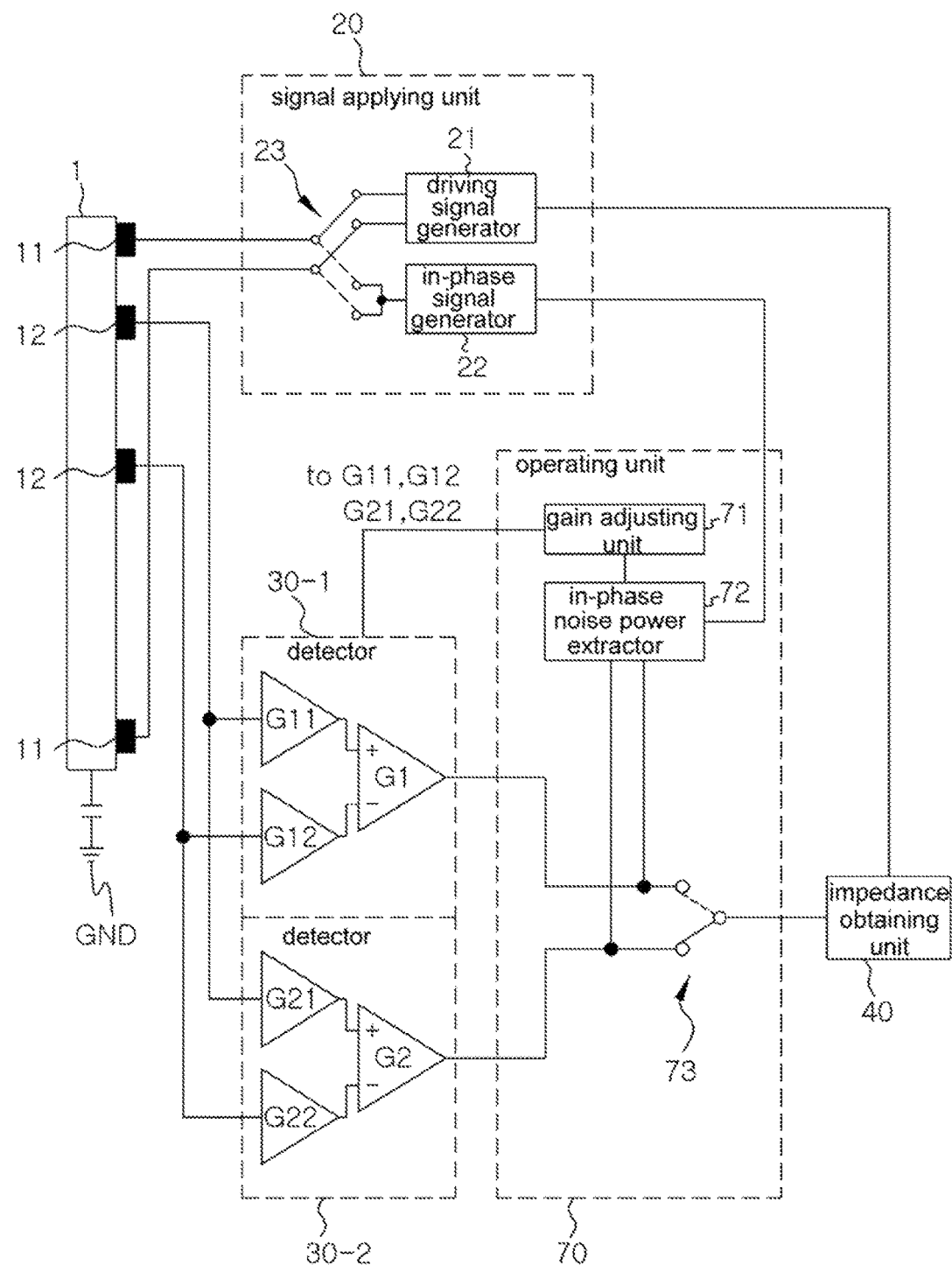
FIG. 5 is a block diagram specifically illustrating an impedance measuring device according to a fourth embodiment of the present invention.

FIG. 5 is a block diagram specifically illustrating an impedance measuring device according to a fourth embodiment of the present invention.

The description of the fourth embodiment of the present invention focuses only on a pair of detectors 30-1 and 30-2 and an operating unit 70, which are components different from those in the first embodiment described in connection with FIG. 2.

Also in the fourth embodiment of the present invention, the detectors 30-1 and 30-2 are provided in pair and are connected in parallel with each other, but without adopting the polarity connection scheme applied in the second and third embodiment, they independently output signals obtained by amplifying signals detected through two sensing electrodes 12 and then differential-operating the amplified signals by differential operators.

An operating unit 70 comprises a gain adjusting unit 70 and an in-phase noise power extractor 72. The in-phase noise power extractor 72 is provided to extract in-phase noise power for each of signals outputted from the pair of detectors 30-1 and 30-2. The operating unit 70 further includes a switch for selecting the more suitable of the signals outputted from the pair of detectors 30-1 and 30-2 and transferring the selected output signal to the impedance obtaining unit 40.

The operating unit 70 configured thus alternately selecting the detectors 30-1 and 30-2 (substantially selecting the output signals) while the signal applying unit 20 applies in-phase signals to the driving electrodes 11 and adjusts the gain of the amplifiers for the selected detector until an in-phase noise relatively lower in power than an in-phase noise mixed with the output signal from the non-selected detector is detected from the output signal from the selected detector. In other words, the gain of the amplifiers is adjusted so that the detector selected at each moment generates and outputs an in-phase noise-suppressed output signal relative to the other detector selected immediately before.

Thereafter, if the signal applying unit 20 stops applying the in-phase signals and applies driving signals to the driving electrodes 11, the switch 73 is operated so that one of the two detectors, which presents relatively less in-phase noise at the time of the in-phase signals being stopped from application, is selected, and the output signal from the selected detector is transferred to the impedance obtaining unit 40.

Meanwhile, when alternately selecting the two detectors 30-1 and 30-2 and adjusting the gain of the amplifiers in the selected detector, the gain of the amplifiers in the other detector which has been selected immediately before and whose gain has been adjusted may be initialized to the gain of the amplifiers in the detector currently selected, and the gain adjustment may then be started, thereby allowing for more exact adjustment as well as a reduction in time for gain adjustment.

Figure 6:
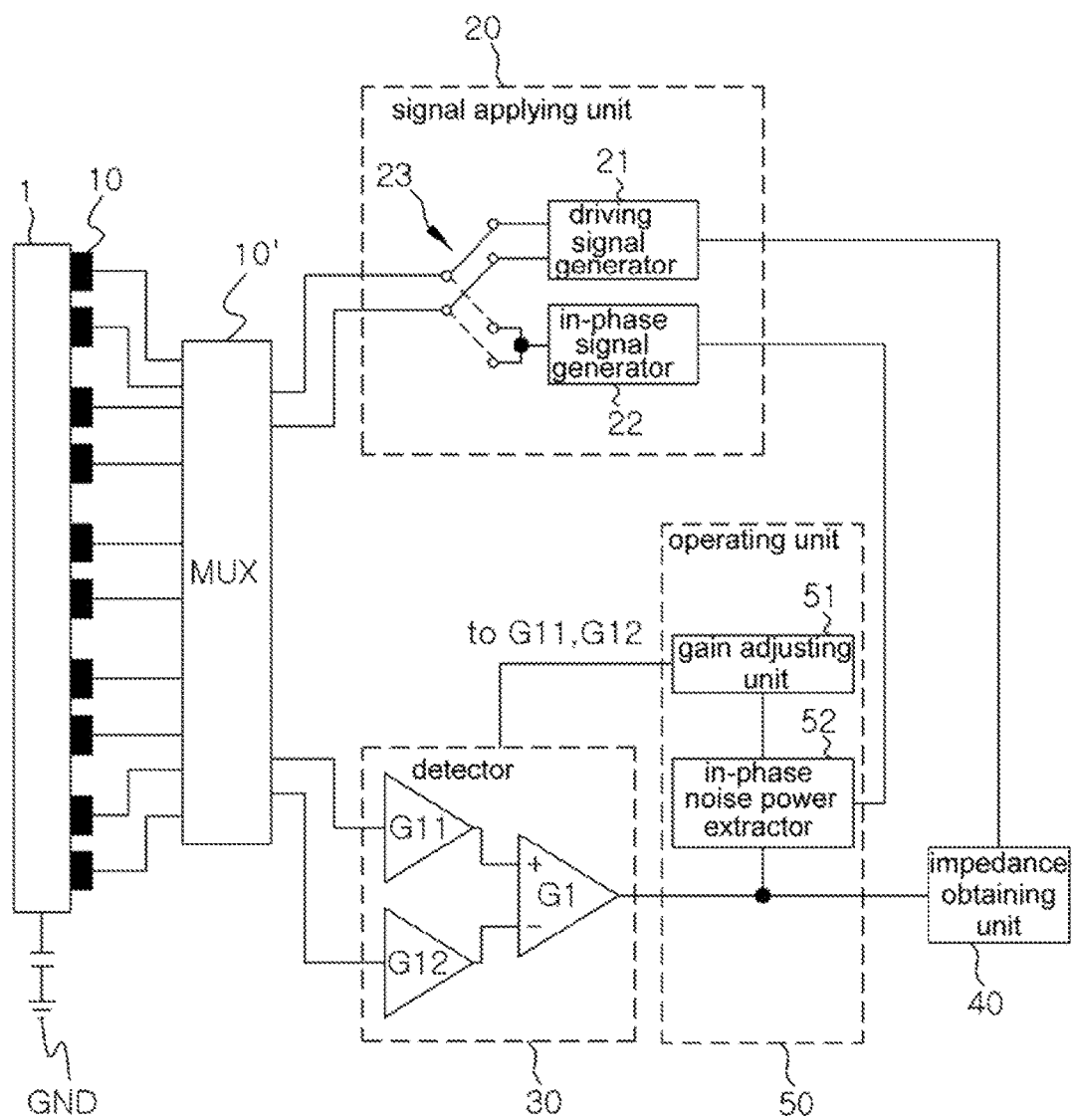
FIG. 6 is a block diagram specifically illustrating an impedance measuring device according to a fifth embodiment of the present invention.

FIG. 6 is a block diagram schematically illustrating an impedance measuring device according to the fifth embodiment of the present invention.

The description of the fifth embodiment of the present invention focuses only on an electrode 10 and a multiplexer 10' for connecting to electrodes which are components distinct from the first embodiment described in connection with FIG. 2.

There are provided a plurality of electrodes 10, each of which is selectively connected to the signal applying unit 20 and the detector 30 by the multiplexer 10'. That is, the multiplexer 10' may select two of the plurality of electrodes 10 as driving electrodes and connect them to the signal applying unit 20 so that in-phase signals and driving signals may sequentially be applied to the connected electrodes. The multiplexer 10' may select two of the plurality of electrodes 10 as sensing electrodes and connect them to the detector 30 so that signals detected through the connected electrodes may be delivered to the detector 30.

Thus, while the plurality of electrodes 10 are spaced apart from each other and contact an object 1, electrodes respectively associated with portions of the object 1 may be selectively used as driving electrodes, and electrodes brought in contact with their corresponding portions may be selectively used, allowing for sequential impedance measurement on several portions of the object 1.

FIG. 7 is a block diagram specifically illustrating an impedance measuring device according to the sixth embodiment of the present invention.

The description of the sixth embodiment of the present invention focuses only on a signal applying unit 20 and operating unit 50 that are components distinct from the first embodiment described in connection with FIG. 1.

The signal applying unit 20 includes a signal synthesizer 24 that simultaneously apply driving signals generated from the driving signal generator 21 and in-phase signals generated from the in-phase signal generator 22 to the driving electrodes 11, with the in-phase signals carried on the driving signals, but the signal applying unit 20 does not include a switch 23 unlike in the first embodiment.

Here, the in-phase signals are signals that are distinct from the driving signals and whose power, although mixed with the driving signals, may be extracted from the mixed signals. For example, in case the driving signals are frequency-swept to have a wider frequency band, the frequency-swept signals except for that of a particular frequency for use as the in-phase signals are used, thus allowing the in-phase noise power extractor 52 of the operating unit 50 to extract the power of a particular frequency component. As another example, signals having a pattern distinct from the driving signals are used as the in-phase signals so that the in-phase noise power extractor 52 of the operating unit 50 may extract the power of an in-phase signal component by correlation analysis.

Thus, mixed signals of signals corresponding to the applied driving signals and in-phase noise corresponding to the applied in-phase signals are detected through the sensing electrodes 12 and transferred to the detector 30.

The in-phase noise power extractor 52 of the operating unit 50 may extract the power of the in-phase signal component, which is distinct from the driving signals, from the signal outputted from the detector 30.

The operating unit 50 is configured to operate as follows.

Before obtaining impedance by the impedance obtaining unit 40 based on the signal outputted from the detector 30, the operating unit 50 operates the in-phase noise power extractor 52 and the gain adjusting unit 51 to extract the power of the in-phase signal component from the output signal of the detector 30 and has a calibration time for adjusting the gain of the amplifiers in the detector 30 to reduce the power of the in-phase signal component.

After the calibration time, the impedance obtaining unit 40 receives the output signal from the detector 30 and obtains the impedance, of course, based on the driving signal component distinct from the in-phase signals.

In another operation scheme, the calibration time might not be defined as a separate limited time.

Specifically, the gain of the amplifiers is adjusted until the power of the in-phase signal component mixed with the output signal of the detector 30 reaches a preset convergence condition, and the output signal of the detector 30 obtained at the time of reaching the convergence condition is used to obtain impedance. Alternatively, the gain of the amplifiers is adjusted while continuously obtaining impedance, and the impedance obtained at the time that the power of the in-phase signal component meets a preset convergence condition is selected.

Here, the convergence condition may include a condition under which the power of the in-phase signal component is reduced to less than a preset power value or a condition under which the power of the in-phase component remains a preset value or less.

Although the operating unit 50 is configured to operate in any way, the output signal of the detector 30 obtained at the time of obtaining impedance is a signal having the in-phase signal component sufficiently removed by calibration, and thus, the exact impedance of the object 1 may be obtained with the contact impedance imbalance between the sensing electrodes 12 and the object 1 and the path impedance imbalance between the sensing electrodes 12 and the detector 30 eliminated.

Meanwhile, it is apparent from a understanding of the embodiments of the present invention that the impedance measuring device using the two detectors 30-1 and 30-2 according to the second and third embodiment or the impedance measuring device using the two detectors 30-1 and 30-2 and the operating unit 70 may also adopt the operation scheme for the multiplexer 10' according to the fifth embodiment or the operation scheme for the signal applying unit 20 and the operating unit 20 according to the sixth embodiment, and no detailed description thereof is presented.

Further, according to the present invention, an impedance imbalance caused per sensing electrode 12 while in-phase signals are applied to the driving electrodes 11 may be eliminated to obtain a noise-freed signal, i.e., a signal generated from the object 1. Thus, the present invention may be used as a device for measuring signals generated from the object 1. In other words, in order to be utilized as a device for measuring biometric signals in case the object 1 is a human body, there may be provided functional keys distinct between an impedance measuring mode and a biometric signal measuring mode, allowing for such a configuration that, in the impedance measuring mode, gain adjustment or normalization condition adjustment is carried out as per the power of in-phase signals and driving signals are then applied to obtain impedance as described above while, in the biometric signal measuring mode, a signal obtained after performing amplification adjustment or normalization condition adjustment as per the power of in-phase signals is treated as a biometric signal.

While the present invention has been shown and described with reference to exemplary embodiments thereof, it will be apparent to those of ordinary skill in the art that various changes in form and detail may be made thereto without departing from the spirit and scope of the present invention as defined by the following claims.

DESCRIPTION OF SYMBOLS

1: Object
10: Electrode
11: Driving electrode, 12: Sensing electrode
10': Multiplexer)
20: Signal applying unit
21: Driving signal generator, 22: In-phase signal generator, 23: Switch
24: Signal synthesizer
30: Detector
40: Impedance obtaining unit
50: Operating unit
51: Gain adjusting unit, 52: In-phase noise power extractor
60: Operating unit
61: Gain adjusting unit, 62: In-phase noise power extractor
63: Power normalizer, 63a: Sub in-phase noise power extractor
63b: Normalizer, 64: In-phase noise suppressor
70: Operating unit
71: Gain adjusting unit, 72: In-phase noise power extractor
73: Switch

What is claimed is:
1. An impedance measuring device, comprising;
   a signal applying unit applying a driving signal for measuring impedance between two driving electrodes spaced apart from each other and contacting an object;
   a detector amplifying, by an amplifier, each of signals detected through two sensing electrodes by applying the driving signal by amplifiers and differential-operating the amplified signal by a differential operator, the two sensing electrodes spaced apart from each other and contacting the object; and
   an impedance obtaining unit outputting impedance of the object corresponding to the two sensing electrodes based on an output signal of the detector,
   wherein the impedance measuring device further comprises an operating unit extracting power of an in-phase noise mixed with the output signal of the detector, adjusting a gain of the amplifier of the detector to decrease the power of the in-phase noise, and then obtaining an impedance based on the output signal of the detector obtained by applying the adjusted gain.

2. The impedance measuring device of claim 1, wherein the signal applying unit sequentially applies an in-phase signal detected as an in-phase noise through the two sensing electrodes and the driving signal for measuring the impedance to the driving electrode, and wherein the operating unit extracts the power of an in-phase signal component from the output signal of the detector when applying the in-phase signal, adjusts the gain of the amplifier of the detector to decrease the power of the in-phase signal component, and then obtains the impedance based on the output signal of the detector when applying the driving signal.

3. The impedance measuring device of claim 1, wherein the signal applying unit simultaneously applies the driving signal for measuring impedance and an in-phase signal that is different from the driving signal and detected as in-phase noise through the two sensing electrodes to the driving electrodes, and wherein the operating unit extracts power of an in-phase signal component from the output signal of the detector, adjusts the gain of the amplifier of the detector to decrease the power of the in-phase signal component, and then obtains impedance based on the driving signal detected as the output signal of the detector.

4. The impedance measuring device of claim 1, wherein the in-phase noise is commercial current frequency component.

5. The impedance measuring device of claim 1, wherein the detector includes a pair of detectors outputting a signal obtained by unequally amplifying the detection signals respectively from the two sensing electrodes by the amplifiers, respectively, and then differential-operating the amplified signals by the differential operator, detection signals relatively highly amplified by the pair of detectors being different from each other, and wherein the operating unit includes a power normalizer normalizing output signals from the pair of detectors so that the power of the in-phase noise becomes the same and an in-phase noise suppressor synthesizing the normalized signals to output an in-phase noise-suppressed signal, wherein the gain of each amplifier in the pair of detectors is adjusted to reduce the power of the in-phase noise remaining on the output signal of the in-phase noise suppressor, and wherein the impedance is obtained based on the signal outputted from the in-phase noise suppressor under application of the adjusted gain and a normalization condition obtained when the gain is adjusted.

6. The impedance measuring device of claim 5,
wherein the in-phase noise suppressor comprises one of a subtractor performing a differential operator and an adder performing addition.

7. The impedance measuring device of claim 1,
wherein the detector comprises two detectors respectively connected to the :sensing electrodes and wherein the operating unit alternately selects the two detectors when adjusting the gain of the amplifier, adjusts the gain of the amplifier in a selected detector until to be lower in in-phase noise of the output signal than an unselected detector, and then selects a detector presenting a relatively lower in-phase noise of the two detectors and obtains the impedance based on the output signal of the selected detector.

\* \* \* \* \*